(12) United States Patent
Chida et al.

(10) Patent No.: US 10,039,890 B2
(45) Date of Patent: Aug. 7, 2018

(54) TOBACCO-FLAVOR-RELEASING MATERIAL AND NON-HEATING TYPE TOBACCO FLAVOR INHALATOR CONTAINING SAME

(71) Applicant: JAPAN TOBACCO INC., Tokyo (JP)

(72) Inventors: Masahiro Chida, Tokyo (JP); Yasuhiro Nakagawa, Tokyo (JP); Tadashi Tatematsu, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 697 days.

(21) Appl. No.: 13/772,101

(22) Filed: Feb. 20, 2013

(65) Prior Publication Data

US 2013/0160779 A1     Jun. 27, 2013

Related U.S. Application Data

(63) Continuation of application No. PCT/JP2011/068457, filed on Aug. 12, 2011.

(30) Foreign Application Priority Data

Aug. 20, 2010 (JP) ................................. 2010-185243

(51) Int. Cl.
    *A24F 47/00*      (2006.01)
    *A61M 15/06*      (2006.01)
    (Continued)

(52) U.S. Cl.
    CPC ............. *A61M 15/06* (2013.01); *A24B 15/14* (2013.01); *A24B 15/283* (2013.01);
    (Continued)

(58) Field of Classification Search
None
See application file for complete search history.

(56) References Cited

U.S. PATENT DOCUMENTS 3,759,270 A * 9/1973 Wright ................... A24D 3/045
                                         131/201
4,291,711 A * 9/1981 Berger ................... A24D 3/043
                                         131/336

(Continued)

FOREIGN PATENT DOCUMENTS

CN        1050493 A      4/1991
CN        1059649 A      3/1992
(Continued)

OTHER PUBLICATIONS

Chinese Office Action dated May 15, 2015 issued in corrsponding Chinese Application No. 201180050572.5 (with English translation).

(Continued)

*Primary Examiner* — Michael J Felton
(74) *Attorney, Agent, or Firm* — Birch, Stewart, Kolasch & Birch, LLP

(57) ABSTRACT

A tobacco-flavor-releasing material includes granules which contain (a) a ground tobacco material, (b) water, (c) a moisturizing agent includes a polyhydric alcohol, (d) at least one pH-adjusting agent selected from the group consisting of potassium carbonate and sodium hydrogencarbonate, and (e) at least one binder selected from the group consisting of pullulan and hydroxypropyl cellulose.

16 Claims, 1 Drawing Sheet

(51) Int. Cl.
  *A24B 15/14* (2006.01)
  *A24B 15/28* (2006.01)
  *A24B 15/30* (2006.01)

(52) U.S. Cl.
  CPC .......... *A24B 15/285* (2013.01); *A24B 15/303* (2013.01); *A24F 47/002* (2013.01)

(56) References Cited

U.S. PATENT DOCUMENTS

| | | | |
|---|---|---|---|
| 4,836,225 A | 6/1989 | Sudoh | |
| 4,924,883 A * | 5/1990 | Perfetti | A24F 47/004 131/335 |
| 4,972,855 A | 11/1990 | Kuriyama et al. | |
| 5,129,408 A | 7/1992 | Jakob et al. | |
| 5,167,242 A | 12/1992 | Turner et al. | |
| 2006/0191548 A1 | 8/2006 | Strickland et al. | |
| 2007/0000505 A1 * | 1/2007 | Zhuang | A24B 15/14 131/342 |
| 2008/0173317 A1 | 7/2008 | Robinson et al. | |
| 2011/0232657 A1 * | 9/2011 | Karles | A24B 15/186 131/275 |

FOREIGN PATENT DOCUMENTS

| | | |
|---|---|---|
| CN | 1144460 A | 3/1997 |
| CN | 1153028 A | 7/1997 |
| CN | 101128130 A | 2/2008 |
| JP | 44-031759 | 12/1969 |
| JP | 63-254974 A | 10/1988 |
| JP | 64-060364 A | 3/1989 |
| JP | 02-002331 A | 1/1990 |
| JP | 6-009497 B2 | 2/1994 |
| JP | 2009-545315 A | 12/2009 |
| WO | WO 2005/046363 A2 | 5/2005 |
| WO | WO 2007/037962 A1 | 4/2007 |
| WO | WO 2009/048522 A1 | 4/2009 |
| WO | WO 2009/087215 A2 | 7/2009 |
| WO | WO 2010/095659 A1 | 8/2010 |

OTHER PUBLICATIONS

Chinese Office Action in Application No. 201180050572.5 dated Nov. 3, 2014 (with English language translation).
Modified Substantive Examination Clear Report for Malaysian Application No. PI 2013000410 dated Nov. 30, 2015.

* cited by examiner

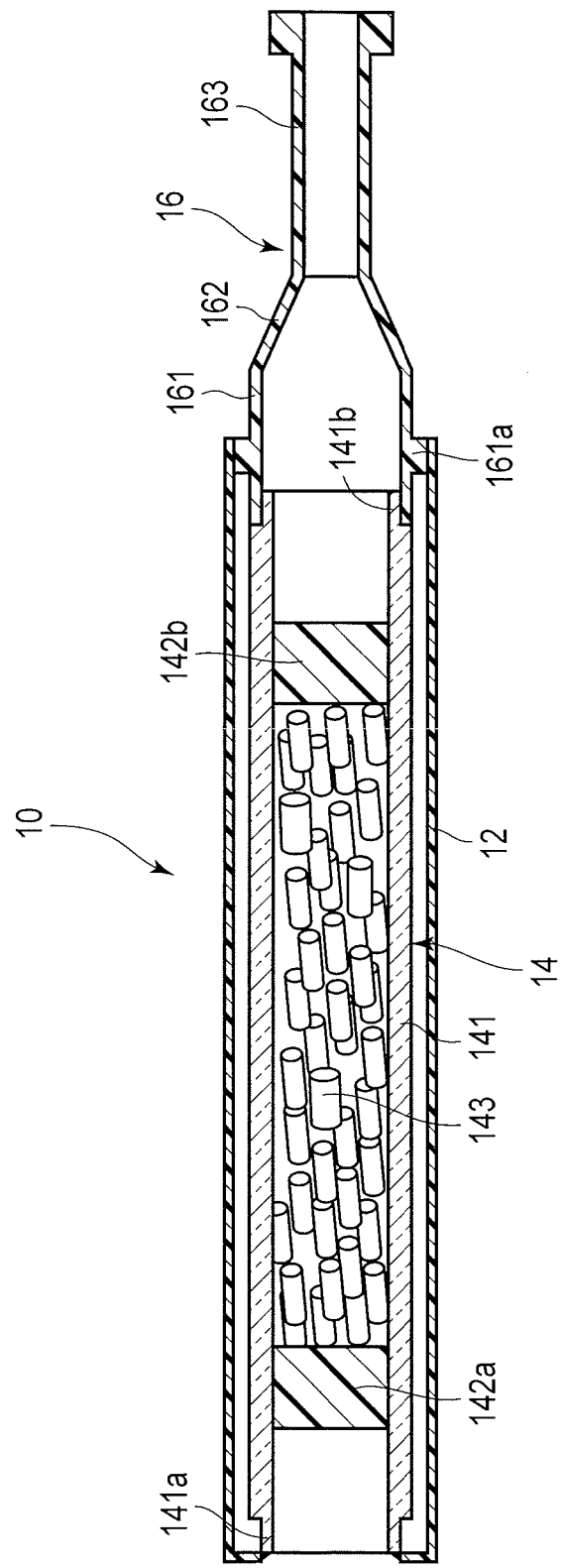

TOBACCO-FLAVOR-RELEASING MATERIAL AND NON-HEATING TYPE TOBACCO FLAVOR INHALATOR CONTAINING SAME

CROSS REFERENCE TO RELATED APPLICATIONS

This application is a Continuation Application of PCT Application No. PCT/JP2011/068457, filed Aug. 12, 2011 and based upon and claiming the benefit of priority from prior Japanese Patent Application No. 2010-185243, filed Aug. 20, 2010, the entire contents of all of which are incorporated herein by reference.

BACKGROUND OF THE INVENTION

1. Field of the Invention

The present invention relates to a tobacco-flavor-releasing material and a non-heating type tobacco flavor inhalator containing the same.

2. Description of the Related Art

A natural tobacco molding in which tobacco flavor is produced without ignition or heating is known from Jpn. Pat. Appln. KOKAI Publication No. 63-254974. The natural tobacco molding is produced by curing small cut pieces of natural tobacco with a cure type resin such as polyurethane or epoxy resin so as to produce a short columnar shape. The natural tobacco molding has a dispersion of fine gaps which are communicating with each other and capable of allowing ventilation by air in the inside. The natural tobacco molding is fitted to one end of a pipe and a user inhales air through the other end to taste the tobacco flavor.

BRIEF SUMMARY OF THE INVENTION

Problem to be Solved by the Invention

However, it has been found that, as for the prior tobacco molding, release of tobacco flavor is insufficient at normal temperature.

Firstly, it is an object of the present invention to provide a tobacco-flavor-releasing material which can release the tobacco flavor at a level satisfactory to a user by bringing the material into contact with the ambient air without heating. Secondly, it is an object of the present invention to provide a non-heating type tobacco flavor inhalator containing the tobacco-flavor-releasing material.

Means for Solving the Problem

In order to solve the above-described problems, the present inventors have been studied. As a result, they have found that a mixture containing a ground tobacco material, a moisturizing agent and a binder is blended with potassium carbonate and/or sodium hydrogencarbonate, and granulated to form granules, with the result that the flavor ingredient contained in the granules is sufficiently released. Potassium carbonate and/or sodium hydrogencarbonate allows the pH of the granules to be adjusted to the alkali side (pH adjustment). Thus, release of tobacco flavor is facilitated.

According to a first aspect of the present invention, there is provided a tobacco-flavor-releasing material comprising granules which contain (a) a ground tobacco material, (b) water, (c) a moisturizing agent comprising a polyhydric alcohol, (d) at least one pH-adjusting agent selected from the group consisting of potassium carbonate and sodium hydrogencarbonate, and (e) at least one binder selected from the group consisting of pullulan and hydroxypropyl cellulose.

According to a second aspect of the present invention, there is provided a non-heating type tobacco flavor inhalator comprising a cylindrical body whose inside is defined by an air flow path where air flows by inhalation, and a tobacco-flavor-releasing material placed in the air flow path, wherein the tobacco-flavor-releasing material comprises the tobacco-flavor-releasing material of the present invention.

Effects of the Invention

The tobacco-flavor-releasing material of the present invention can release the tobacco flavor at a level satisfactory to a user by bringing the material into contact with the ambient air without heating. According to the non-heating type tobacco flavor inhalator of the present invention, the user can taste the tobacco flavor merely by inhaling the ambient air without heating.

BRIEF DESCRIPTION OF THE SEVERAL VIEWS OF THE DRAWING

The single FIGURE is an enlarged cross-sectional view showing a tobacco flavor inhalator according to an embodiment of the present invention.

DETAILED DESCRIPTION OF THE INVENTION

Hereinafter, the embodiments of the present invention will be explained in detail.

According to an aspect of the present invention, there is provided a tobacco-flavor-releasing material. The tobacco-flavor-releasing material contains tobacco-flavor-releasing granules. The tobacco-flavor-releasing granule contains (a) a ground tobacco material, (b) water, (c) a moisturizing agent comprising a polyhydric alcohol, (d) at least one pH-adjusting agent selected from the group consisting of potassium carbonate and sodium hydrogencarbonate, and (e) at least one binder selected from the group consisting of pullulan and hydroxypropyl cellulose. The tobacco-flavor-releasing granule of the present invention can release the flavor ingredient contained therein from the granule by bringing it into contact with the ambient air without heating. Therefore, for example, a hollow container whose both opening ends are sealed with breathable filters is filled with the tobacco-flavor-releasing granules of the present invention and the user inhales the ambient air through one end of the container, and thereby the user can taste the tobacco flavor.

The ground tobacco material (ingredient (a)) contained in the tobacco-flavor-releasing granule of the present invention releases tobacco flavor and contains ground tobacco leaves, ground reconstituted tobacco and the like. Tobacco types include burley, flue-cured, and oriental tobacco. The tobacco material is preferably ground into a size of 10 to 90 μm.

The raw material mixture of the tobacco-flavor-releasing granule of the present invention usually contains a ground tobacco material in an amount of 20 to 80% by weight. If the amount of the tobacco material is less than 20% by weight, the release of the tobacco flavor may become insufficient under non-heating conditions (at ambient temperature). If the amount of the tobacco material exceeds 80% by weight, the integrity of the granule may not be maintained.

The water (ingredient (b)) contained in the tobacco-flavor-releasing granule of the present invention maintains the integrity of the granule. If the water is not contained, the granule is easily broken, and furthermore the release of a flavor contained in the granule is reduced.

The raw material mixture of the tobacco-flavor-releasing granule of the present invention usually contains water in an amount of 3 to 13% by weight. The tobacco-flavor-releasing granule of the present invention may usually contain water so that the drying loss is from 5 to 17% by weight. The term "drying loss" in the present invention means changes in weight before and after drying when an aliquot of a sample is taken for measurement and the total water in the sample is evaporated to completely dry the sample (for example, when dried at a constant temperature [105° C.] for 15 minutes). Specifically, it means a ratio (% y eight) of the total of the amount of water contained in the sample and the amount of volatile components which volatilize under the drying conditions to the sample weight. That is, the drying loss (% by weight) can be represented by the following equation:

Drying loss (% by weight)={(weight of sample before complete drying)−(weight of sample after complete drying)}×100/weight of sample before complete drying.

The moisturizing agent (ingredient (c)) contained in the tobacco-flavor-releasing granule of the present invention protects the granule from being dried with time and retains water in the granule. The moisturizing agent comprises polyhydric alcohol. The polyhydric alcohol includes glycerin, propylene glycol, sorbitol, xylitol, and erythritol. These polyhydric alcohols may be used alone or in combination with two or more thereof.

The raw material mixture of the tobacco-flavor-releasing granule of the present invention may usually contain the moisturizing agent in an amount of 5 to 15% by weight. If the amount of the moisturizing agent is less than 5% by weight, the water is not sufficiently retained. On the other hand, even if the amount of the moisturizing agent exceeds 15% by weight, improvement in effects is not particularly observed.

The pH-adjusting agent (ingredient (d)) contained in the tobacco-flavor-releasing granule comprises potassium carbonate, sodium hydrogencarbonate or a mixture thereof. The pH-adjusting agent allows the pH of the tobacco-flavor-releasing granule to be adjusted to the alkali side. Such pH adjustment facilitates release of the flavor ingredient contained in the tobacco-flavor-releasing granule from the granule, and thereby the smoking taste satisfied by the user is provided.

The raw material mixture of the tobacco-flavor-releasing granule of the present invention may usually contain the pH-adjusting agent in an amount of 5 to 20% by weight. If the amount of the pH-adjusting agent is less than 5% by weight, the flavor release is not sufficiently facilitated. On the other hand, even if the amount of the pH-adjusting agent exceeds 20% by weight, the flavor release is not further improved.

The binder (ingredient (e)) contained in the tobacco-flavor-releasing granule of the present invention binds the granule ingredients to maintain the integrity of the granule. The binder comprises pullulan, hydroxypropyl cellulose (HPC) or a mixture thereof. Other binders do not have a good flavor.

The raw material mixture of the tobacco-flavor-releasing granule of the present invention may usually contain the binder in an amount of 0.5 to 15% by weight. If the amount of the binder is less than 0.5% by weight, the binding effect is not sufficiently exerted. On the other hand, if the amount of the binder exceeds 15% by weight, the flavor release may be reduced.

Tobacco-flavor-releasing granule of the present invention may comprise the ingredients (a), (b), (c), (d) and (e). Further, it may include an additional ingredient.

The additional ingredient includes (f) a flavor material (in solid or liquid form) other than the tobacco flavor. The flavor material includes sugar (for example, sucrose and fructose), cocoa powder, carob powder, coriander powder, licorice powder, orange peel powder, rose hip powder, chamomile flower powder, lemon verbena powder, peppermint powder, leaf powder, spearmint powder, black tea powder, and menthol.

The raw material mixture of the tobacco-flavor-releasing granule of the present invention may usually contain the flavor material in an amount of 0.5 to 45% by weight. The flavor material may be added to the ingredients (a), (b), (c), (d) and (e) by directly kneading the flavor material with the ingredients. Alternatively, the flavor material may be added to the ingredients by carrying the flavor material on a known inclusion host compound such as cyclodextrin to prepare an inclusion compound and kneading it with the ingredients.

When the tobacco-flavor-releasing granule of the present invention consists of the ingredients (a), (b), (c), (d) and (e), the raw material mixture of the tobacco-flavor-releasing granule may usually contain the ingredient (a) in an amount of about 33% by weight or more (and about 80% by weight or less).

When the tobacco-flavor-releasing granule of the present invention comprises the ingredients (a), (b), (c), (d) and (e), the granule can be produced from a raw material mixture containing:

34 to 81% by weight of (a) a ground tobacco material,
3.8 to 16% by weight of (b) water,
5 to 19% by weight of (c) a moisturizing agent comprising a polyhydric alcohol,
5 to 22% by weight of (d) at least one pH-adjusting agent selected from the group consisting of potassium carbonate and sodium hydrogencarbonate, and
0.7 to 18% by weight of (e) at least one binder selected from the group consisting of pullulan and hydroxypropyl cellulose. As described above, the produced tobacco-flavor-releasing granule of the present invention can have a drying loss of 5 to 17% by weight, generally when dried by heating at 105° C. for 15 minutes.

When the tobacco-flavor-releasing granule of the present invention comprises the ingredients (a), (b), (c), (d), (e) and (f), the granule can be produced from a raw material mixture containing:

20 to 60% by weight of (a) a ground tobacco material,
3 to 13% by weight of (b) water,
5 to 15% by weight of (c) a moisturizing agent comprising a polyhydric alcohol,
5 to 20% by weight of (d) at least one pH-adjusting agent selected from the group consisting of potassium carbonate and sodium hydrogencarbonate,
0.5 to 15% by weight of (e) at least one binder selected from the group consisting of pullulan and hydroxypropyl cellulose, and
2 to 42% by weight of (f) a flavor material other than tobacco flavor. As described above, the produced tobacco-flavor-releasing granule of the present invention can have a drying loss of 5 to 17% by weight, generally when dried by heating at 105° C. for 15 minutes.

In order to produce the tobacco-flavor-releasing granule of the present invention, the ingredients (a), (c), (d) and (e), and if necessary, the ingredient (f) are mixed, and the ingredient (b) is added to the mixture and kneaded. The obtained kneaded product is granulated with a wet extrusion granulator (a long column shape), and then the granule size is regulated so as to have a short column shape or a spherical shape. The average grain diameter (D50) of the obtained granules is usually from 0.3 to 1.2 mm.

In the extrusion granulation process, the kneaded product is preferably extruded under a pressure of 2 kN or more at ambient temperature. As a result of the extrusion under the high pressure, the temperature of the kneaded product increases at an outlet of the extrusion granulator from ambient temperature to, for example, the range of 90 to 100° C. instantly and rapidly. The increase in the temperature of the kneaded product evaporates water and volatile components in a total amount of 2 to 4% by weight. Therefore, the amount of the water to be added to produce the kneaded product may be larger than a desired water content contained in the granules (i.e., an end product) by the evaporation amount.

The granules obtained by extrusion granulation may be further dried, if necessary, to adjust the water content contained in the granules. For example, when the drying loss of the granules obtained by extrusion granulation is measured and it is larger than the desired drying loss (for example, 5 to 17% by weight), the granules may be further dried to obtain the desired drying loss. The drying conditions (temperature and time) which are necessary to decrease the drying loss by a predetermined value are determined in advance, and then the drying conditions (temperature and time) for obtaining the desired drying loss can be set based on the conditions determined in advance.

The tobacco-flavor-releasing material of the present invention may consist of only the tobacco-flavor-releasing granules or may further contain an additional tobacco material other than the granules.

The additional tobacco material is usually tobacco leaf shreds or fine powder. The additional tobacco material may be used by mixing it with the tobacco-flavor-releasing granules of the present invention.

The tobacco-flavor-releasing material of the present invention may contain 50% by weight or more of the tobacco-flavor-releasing granules of the present invention and less than 50% by weight of the additional tobacco material. Preferably, the tobacco-flavor-releasing material of the present invention contains 60 to 90% by weight of the tobacco-flavor-releasing granules of the present invention and 10 to 40% by weight of the additional tobacco material. A part or all of the additional tobacco material may be replaced with an additional flavor material other than tobacco, such as finely cut orange peel, finely cut rose hip, finely cut chamomile flower, finely cut lemon verbena, vanilla bean, finely cut peppermint leaves, finely cut spearmint, finely cut black tea leaves, and finely cut rose flower. When all of the additional tobacco material is replaced with the additional flavor material, the tobacco-flavor-releasing material of the present invention may contain the additional flavor material in an amount of less than 50% by weight. When the part of the additional tobacco material is replaced with the additional flavor material, the tobacco-flavor-releasing material of the present invention may contain the additional flavor material in an amount of not more than 5% by weight.

According to another aspect of the present invention, there is provided a non-heating type tobacco flavor inhalator. The non-heating type tobacco flavor inhalator comprises a cylindrical body whose inside is defined by an air flow path where air flows by inhalation, and a tobacco-flavor-releasing material placed in the air flow path, wherein the tobacco-flavor-releasing material comprises the tobacco-flavor-releasing material of the present invention. In an embodiment, the non-heating type tobacco flavor inhalator comprises a cartridge comprising a cylindrical container filled with the tobacco-flavor-releasing material, and the cartridge is placed in the air flow path.

FIG. 1 is an enlarged cross-sectional view showing an example of a non-heating type tobacco flavor inhalator 10 which contains a tobacco-flavor-releasing material according to an embodiment of the present invention.

The non-heating type tobacco flavor inhalator 10 comprises a holder 12 which is a cylindrical body. Since the holder 12 is cylindrical, ambient air may be passed through the inside of the holder (namely, the inside of the holder is defined by the air flow path). For example, although the inner wall surface of the holder 12 is circular, the external wall surface may have a rounded square shape. The holder 12 is formed by using, for example, plastics and it may be black-colored.

A cartridge 14 is placed in the holder 12. The cartridge 14 comprises a cylindrical container 141 having an outer diameter slightly smaller than the inner diameter of the holder 12. Breathable filters 142a and 142b are placed at a position slightly distant from the distal and proximal ends of the cylindrical container 141 toward the inside. The space in the cylindrical container 141, which is defined by the two filters 142a and 142b, is filled with the tobacco-flavor-releasing material 143 of the present invention. The distal and proximal ends of the cylindrical container 141 are configured to have thin-walled portions 141a and 141b. The cylindrical container 141 may be made of plastics. For example, it may be transparent. The cylindrical container 141 may have the same length and diameter as those of a normal cigarette rod. For example, the cylindrical container 141 may have an inner diameter of 6 to 9 mm and a length of 50 to 70 mm. The filters 142a and 142b may be made of pulp or cellulose acetate. More specifically, the filters 142a and 142b may be formed by crepe-processing a piece of paper of pulp and weaving it into a web form. Alternatively, the filters 142a and 142b may be formed using a nonwoven fabric of pulp or may be formed using a cellulose acetate fiber bundle. The cylindrical container 141 having the above-described size may be filled with 0.3 g to 1.0 g of the tobacco-flavor-releasing material 143 containing the tobacco-flavor-releasing granules of the present invention. As described above, the tobacco-flavor-releasing material 143 may consist of the tobacco-flavor-releasing granules or may include the additional tobacco material or the additional flavor material.

A mouthpiece 16 is attached to the proximal end of the cylindrical container 141. The mouthpiece 16 includes a cylindrical portion 161 having an inner diameter almost equal to an outer diameter of the thin-walled portion 141b of the cylindrical container 141 and a flat hollow portion 163 which is connected to the cylindrical portion 161 through a transition portion 162. The flat hollow portion 163 is a portion which is inserted into a user's mouth. The cylindrical portion 161 has an annular projection 161a that engages with the inner surface of the proximal end of the holder 12 on the outer periphery surface. The mouthpiece 16 may be made of plastics. For example, it may be black-colored. The cylindrical portion 161 can be attached to the cylindrical container 141 by fitting the end of the cylindrical portion 161 to the thin-walled portion 141b at the proximal end of the cylindrical container 141. The holder 12 and the mouthpiece 16 can be freely attached and detached in rotation lock mode.

When it is used, the mouthpiece 16 is attached to the cartridge 14, the cartridge 14 is inserted into the holder 12, and it is locked by rotation. Then, the user inhales the ambient air through the mouthpiece 16. The inhaled ambient air enters the cartridge through the filter 142a, comes into contact with the tobacco-flavor-releasing material 143, passes through the filter 142b along with the flavor from the tobacco-flavor-releasing material 143, and enters a user's mouth through the inside of the mouthpiece 16, and thereby the user can taste the flavor.

As described above, the non-heating type tobacco flavor inhalator is suitably filled with the tobacco-flavor-releasing material of the present invention to taste the tobacco flavor. However, the tobacco-flavor-releasing material of the present invention may be used as a flavor-releasing material in a non-combustive smoking article which comprises a flavor-releasing portion containing the flavor-releasing material generating flavor by heating and a heat source heating the flavor-releasing material by heat of combustion positioning at the end of the flavor-releasing portion separately from the flavor-releasing portion. The tobacco-flavor-releasing material of the present invention may be applied to tobacco products other than the above products.

EXAMPLES

Examples 1 to 26

In the examples, the ingredients shown in Table 1 below were used as raw materials. Among these ingredients, the tobacco leaf powder and the flavor material were ground into an average grain diameter of 30 to 50 μm in advance. These ingredients were uniformly kneaded and the obtained kneaded product was granulated using a wet extrusion granulator (MultiGran MG-55, manufactured by Dalton Corp.; mesh size: 0.7 mm). In Example 24, commercially available β-cyclodextrin-included menthol powder (menthol inclusion compound) was prepared as the flavor material. The powder was mixed with other materials to form granules. The extrusion pressure was 2.5±0.2 kN. The grain size of the obtained granulated product was regulated using a grinding-type molding machine (Marumerizer Q-230T, manufactured by Dalton Corp.). The granules after the grain size regulation were spread on a sieve having 60 meshes and a diameter of 20 cm and dried for about 5 minutes using a constant temperature blowing drier (DK63, manufactured by Yamato Scientific Co., Ltd.) which was preset to 40° C. so as to have a final drying loss of 14 to 15% by weight.

The drying loss was determined by heating some granules (1.5 g) at 105° C. for 15 minutes to completely dry them, measuring changes in weight by a halogen moisture analyzer (HR73, manufactured by Mettler), and calculating according to the following equation:

Drying loss (% by weight)={(weight of granules before complete drying)−(weight of granules after complete drying)}×100/weight of granules before complete drying.

As described above, "tobacco-flavor-releasing granules" having an average grain diameter (D50) of 0.7 mm were obtained by drying the granules at 40° C. for about 5 minutes. The irritating odor and tobacco smoking taste were evaluated by 7 in-house male panelists aged 32 to 52 based on the following criteria.

<Irritating Odor>
1: Almost none;
2: Slight irritating odor;
3: Weak irritating odor;
4: Strong irritating odor; and
5: Considerably strong irritating odor.

<Tobacco Smoking Taste>
× (Bad): Unpleasant taste is accompanied and tobacco flavor is not emitted;
Δ (Poor): Tobacco flavor is emitted, but unpleasant taste is accompanied;
◯ (Good): Tobacco flavor is emitted; and
⊙ (Excellent): Tobacco flavor is well emitted.

About 20 g of each sample (tobacco-flavor-releasing granules) was put into a 100 g capacity glass beaker, and it was used as a sample for evaluating irritating odor. The irritating odor was twice evaluated by each panelist. The non-heating type tobacco flavor inhalator having the structure shown in FIG. 1 was filled with each sample (tobacco-flavor-releasing granules). Each panelist inhaled it to evaluate the tobacco smoking taste. Here, the cylindrical container 141 having an inner diameter of 8 mm and a length of 50 mm was filled with 0.5 g of the tobacco-flavor-releasing granules. As for the irritating odor, the most frequently occurring value in all 14 data (twice/panelist×7 panelists) was defined as an evaluation value of the irritating odor of each sample. As for the tobacco smoking taste, the most frequently occurring result in all 7 data (once/panelist×7 panelists) was defined as an evaluation result of the tobacco smoking taste of each sample. These sensory evaluation results are shown in Table 1.

TABLE 1

| Example | Tobacco leaf powder | | Flavor material | | | | | | pH adjusting agent | |
|---|---|---|---|---|---|---|---|---|---|---|
| | Burley tobacco | Flue-cured tobacco | Cocoa powder | Sucrose | Carob powder | Coriander powder | Chamomile flower powder | Menthol inclusion compound | Potassium carbonate | Sodium hydrogencarbonate |
| 1 | 414 g | — | 206 g | — | — | — | — | — | 100 g | — |
| 2 | — | 414 g | 206 g | — | — | — | — | — | 100 g | — |
| 3 | 414 g | — | — | 206 g | — | — | — | — | 100 g | — |
| 4 | — | 414 g | — | 206 g | — | — | — | — | 100 g | — |
| 5 | 414 g | — | — | — | 206 g | — | — | — | 100 g | — |
| 6 | — | 414 g | — | — | 206 g | — | — | — | 100 g | — |
| 7 | 560 g | — | — | — | — | 60 g | — | — | — | 100 g |
| 8 | — | 560 g | — | — | — | 60 g | — | — | — | 100 g |
| 9 | 414 g | — | — | 206 g | — | — | — | — | 100 g | — |
| 10 | 414 g | — | — | 186 g | — | — | 20 g | — | 100 g | — |
| 11 | 200 g | — | — | 420 g | — | — | — | — | 100 g | — |

TABLE 1-continued

| | | | | | | | | | | |
|---|---|---|---|---|---|---|---|---|---|---|
| 12 | — | 200 g | — | — | 420 g | — | — | — | 100 g | — |
| 13 | 600 g | — | — | — | 20 g | — | — | — | 100 g | — |
| 14 | — | 600 g | — | — | 20 g | — | — | — | 100 g | — |
| 15 | 414 g | — | — | — | 206 g | — | — | — | 100 g | — |
| 16 | 414 g | — | — | — | 206 g | — | — | — | 100 g | — |
| 17 | 414 g | — | — | — | 281 g | — | — | — | 100 g | — |
| 18 | 414 g | — | — | — | 156 g | — | — | — | 100 g | — |
| 19 | 414 g | — | — | — | 256 g | — | — | — | 50 g | — |
| 20 | 414 g | — | — | — | 106 g | — | — | — | 200 g | — |
| 21 | — | 414 g | — | — | 256 g | — | — | — | 50 g | — |
| 22 | — | 414 g | — | — | 106 g | — | — | — | 200 g | — |
| 23 | 810 g | — | — | — | — | — | — | — | 50 g | — |
| 24 | 414 g | — | — | — | 196 g | — | — | 10 g | 100 g | — |
| 25 | 464 g | — | — | — | 256 g | — | — | — | — | — |
| 26 | — | 464 g | — | — | 256 g | — | — | — | — | — |

| Example | Binder Pullulan | Binder HPC | Moisturizing agent Glycerin | Water | Total | Sensory evaluation Irritating odor | Sensory evaluation Tobacco smoking taste |
|---|---|---|---|---|---|---|---|
| 1 | 100 g | — | 100 g | 80 g | 1000 g | 2 | ○ |
| 2 | 100 g | — | 100 g | 80 g | 1000 g | 1 | Δ |
| 3 | 100 g | — | 100 g | 80 g | 1000 g | 3 | ○ |
| 4 | 100 g | — | 100 g | 80 g | 1000 g | 3 | Δ |
| 5 | — | 100 g | 100 g | 80 g | 1000 g | 2 | ⊚ |
| 6 | — | 100 g | 100 g | 80 g | 1000 g | 1 | ○ |
| 7 | — | 100 g | 100 g | 80 g | 1000 g | 1 | ○ |
| 8 | — | 100 g | 100 g | 80 g | 1000 g | 1 | ○ |
| 9 | — | 100 g | 100 g | 80 g | 1000 g | 2 | ⊚ |
| 10 | — | 100 g | 100 g | 80 g | 1000 g | 2 | ⊚ |
| 11 | — | 100 g | 100 g | 80 g | 1000 g | 1 | ○~Δ |
| 12 | — | 100 g | 100 g | 80 g | 1000 g | 1 | ○~Δ |
| 13 | — | 100 g | 100 g | 80 g | 1000 g | 4 | Δ |
| 14 | — | 100 g | 100 g | 80 g | 1000 g | 2 | ○ |
| 15 | — | 100 g | 50 g | 130 g | 1000 g | 2 | Δ |
| 16 | — | 100 g | 150 g | 30 g | 1000 g | 3 | ⊚ |
| 17 | 5 g | — | 100 g | 100 g | 1000 g | 2 | ⊚ |
| 18 | — | 150 g | 100 g | 80 g | 1000 g | 2 | Δ |
| 19 | — | 100 g | 100 g | 80 g | 1000 g | 2 | ⊚ |
| 20 | — | 100 g | 100 g | 80 g | 1000 g | 3 | Δ |
| 21 | — | 100 g | 100 g | 80 g | 1000 g | 1 | ○ |
| 22 | — | 100 g | 100 g | 80 g | 1000 g | 3 | ○ |
| 23 | — | 50 g | 50 g | 40 g | 1000 g | 3 | ○ |
| 24 | — | 100 g | 100 g | 80 g | 1000 g | 2 | ○~Δ |
| 25 | — | 100 g | 100 g | 80 g | 1000 g | 1 | X |
| 26 | — | 100 g | 100 g | 80 g | 1000 g | 1 | X |

As shown in Table 1, the granules (tobacco-flavor-releasing granules of the present invention) of Examples 1 to 24 containing potassium carbonate or sodium hydrogencarbonate as the pH-adjusting agent are excellent in tobacco smoking taste as compared with the granules of Examples 25 and 26 not containing the pH-adjusting agent.

Examples 27 to 34

As shown in Table 2 below, tobacco-flavor-releasing materials were prepared by uniformly mixing the "tobacco-flavor-releasing granules" produced in Example 5 with the additional tobacco material, the additional flavor material other than tobacco or a mixture thereof. The additional tobacco material (Flue-cured tobacco leaf shreds) and the additional flavor material were cut into a length of 2 to 3 mm in advance. The irritating odor and tobacco smoking taste of the obtained tobacco-flavor-releasing materials were evaluated in the same manner as Examples 1 to 26. The results are shown in Table 2.

TABLE 2

| Example | Flavor-releasing granules of Example 5 | Additional tobacco material Flue-cured tobacco leaf shreds | Additional flavor material other than tobacco Finely cut chamomile flower | Additional flavor material other than tobacco Finely cut orange peel | Sensory evaluation Irritating odor | Sensory evaluation Tobacco smoking taste |
|---|---|---|---|---|---|---|
| 27 | 90 part by weight | 10 part by weight | — | — | 2 | ○ |
| 28 | 80 part by weight | 20 part by weight | — | — | 2 | ⊚ |
| 29 | 70 part by weight | 30 part by weight | — | — | 2 | ⊚ |
| 30 | 60 part by weight | 40 part by weight | — | — | 1 | ○ |
| 31 | 75 part by weight | 20 part by weight | 5 part by weight | — | 1 | ○ |
| 32 | 75 part by weight | 20 part by weight | — | 5 part by weight | 1 | ⊚ |

TABLE 2-continued

| Example | Flavor-releasing granules of Example 5 | Additional tobacco material Flue-cured tobacco leaf shreds | Additional flavor material other than tobacco | | Sensory evaluation | |
|---|---|---|---|---|---|---|
| | | | Finely cut chamomile flower | Finely cut orange peel | Irritating odor | Tobacco smoking taste |
| 33 | 80 part by weight | — | 20 part by weight | — | 2 | ○~Δ |
| 34 | 80 part by weight | — | — | 20 part by weight | 2 | ○~Δ |

As described above, when the tobacco-flavor-releasing material of the present invention is brought into contact with air at ambient temperature, the user can sufficiently taste the tobacco smoking taste. Additionally, the released flavor has little irritating odor.

DESCRIPTION OF REFERENCE NUMBERS

10 . . . Non-heating type tobacco flavor inhalator
12 . . . Holder
14 . . . Cartridge
141 . . . Cylindrical container
141a, 141b . . . Thin-walled portion
142a, 142b . . . Filter
143 . . . Tobacco-flavor-releasing material
16 . . . Mouthpiece
161 . . . Cylindrical portion of the mouthpiece
161a . . . Annular projection
162 . . . Transition portion of the mouthpiece
163 . . . Flat hollow portion of the mouthpiece

What is claimed is:

1. A non-heating type tobacco flavor inhalator comprising:
   a plastic hollow cylindrical body forming the non-heating type tobacco flavor inhalator, said plastic hollow cylindrical body having an air inflow end and an air outflow end and an air flow path extending from the air inflow end to the air outflow end wherein air flows by inhalation;
   a first filter placed in the air flow path, the first filter directly communicating with the outside of the non-heating type tobacco flavor inhalator through the air inflow end;
   a second filter placed in the air flow path between the air outflow end and the first filter;
   a tobacco-flavor-releasing material placed in the air flow path between the first and second filters; and
   a mouth piece disposed at the air outflow end,
   wherein the tobacco-flavor-releasing material comprises granules which contain:
   (a) a ground tobacco material,
   (b) water,
   (c) a moisturizing agent comprising a polyhydric alcohol,
   (d) at least one pH-adjusting agent selected from the group consisting of potassium carbonate and sodium hydrogencarbonate, and
   (e) at least one binder selected from the group consisting of pullulan and hydroxypropyl cellulose.

2. The non-heating type tobacco flavor inhalator according to claim 1, wherein the tobacco-flavor-releasing material includes tobacco leaves.

3. The non-heating type tobacco flavor inhalator according to claim 1, wherein the polyhydric alcohol is selected from the group consisting of gylcerin, propylene glycol, sorbitol, xylitol and erythritol.

4. The non-heating type tobacco flavor inhalator according to claim 1, wherein the granules contain a flavor material other than tobacco.

5. The non-heating type tobacco flavor inhalator according to claim 4, wherein the flavor material other than tobacco is carried by an inclusion host compound which forms an inclusion compound with the flavor material.

6. The non-heating type tobacco flavor inhalator according to claim 1, wherein the tobacco-flavor-releasing material further comprises an additional tobacco material in addition to the granules.

7. The non-heating type tobacco flavor inhalator according to claim 1, wherein the tobacco-flavor-releasing material further comprises an additional flavor material other than tobacco in addition to the granules.

8. The non-heating type tobacco flavor inhalator according to claim 1, wherein the granules are produced from a raw material mixture which contains:
   34 to 81% by weight of (a) a ground tobacco material,
   3.8 to 16% by weight of (b) water,
   5 to 19% by weight of (c) a moisturizing agent comprising a polyhydric alcohol,
   5 to 22% by weight of (d) at least one pH-adjusting agent selected from the group consisting of potassium carbonate and sodium hydrogencarbonate,
   0.7 to 18% by weight of (e) at least one binder selected from the group consisting of pullulan and hydroxypropyl cellulose, and
   the granules have a drying loss of 5 to 17% by weight when dried by heating at 105° C. for 15 minutes.

9. A non-heating type tobacco flavor inhalator comprising:
   a plastic hollow cylindrical body forming the non-heating type tobacco flavor inhalator, said plastic hollow cylindrical body having an air inflow end and an air outflow end and an air flow path extending from the air inflow end to the air outflow end wherein air flows by inhalation,
   a first filter placed in the air flow path at a position recessed from the air inflow end, the first filter being adjacent to an air-filled space in the air flow path, the air-filled space communicating with an outside of the non-heating type tobacco flavor inhalator through the air inflow end;
   a second filter placed in the air flow path between the air outflow end and the first filter;
   a tobacco-flavor-releasing material placed in the air flow path between the first and second filters; and,
   a mouth piece disposed at the air outflow end,
   wherein the tobacco-flavor-releasing material comprises granules which contain:
   (a) a ground tobacco material,
   (b) water,
   (c) a moisturizing agent comprising a polyhydric alcohol, (d) at least one pH-adjusting agent selected from the group consisting of potassium carbonate and sodium hydrogencarbonate, and (e) at least one binder selected from the group consisting of pullulan and hydroxypropyl cellulose.

10. The non-heating type tobacco flavor inhalator according to claim 9, wherein the tobacco-flavor-releasing material includes tobacco leaves.

11. The non-heating type tobacco flavor inhalator according to claim 9, wherein the polyhydric alcohol is selected from the group consisting of glycerin, propylene glycol, Sorbitol, xylitol and erythritol.

12. The non-heating type tobacco flavor inhalator according to claim 9, wherein the granules contain a flavor material other than tobacco.

13. The non-heating type tobacco flavor inhalator according to claim 12, wherein the flavor material other than tobacco is carried by an inclusion host compound which forms an inclusion compound with the flavor material.

14. The non-heating type tobacco flavor inhalator according to claim 9, wherein the tobacco-flavor-releasing material further comprises an additional tobacco material in addition to the granules.

15. The non-heating type tobacco flavor inhalator according to claim 9, wherein the tobacco-flavor-releasing material further comprises an additional flavor material other than tobacco in addition to the granules.

16. The non-heating type tobacco flavor inhalator according to claim 9, wherein the granules are produced from a raw material mixture which contains:

34 to 81% by weight of (a) a ground tobacco material, 3.8 to 16% by weight of (b) water, 5 to 19% by weight of (c) a moisturizing agent comprising a polyhydric alcohol, 5 to 22% by weight of (d) at least one pH-adjusting agent selected from the group consisting of potassium carbonate and sodium hydrogencarbonate, and 0.7 to 18% by weight of (e) at least one binder selected from the group consisting of pullulan and hydroxypropyl cellulose; and the granules have a drying loss of 5 to 17% by weight when dried by heating at 105° C. for 15 minutes.

* * * * *